United States Patent [19]

Karasaki

[11] 4,421,410

[45] Dec. 20, 1983

[54] METHOD AND APPARATUS FOR INSPECTING PRINTED WIRING BOARDS

[75] Inventor: Koichi Karasaki, Hadano, Japan

[73] Assignee: Hitachi, Ltd., Tokyo, Japan

[21] Appl. No.: 171,265

[22] Filed: Jul. 22, 1980

[30] Foreign Application Priority Data

Jul. 23, 1979 [JP] Japan .................................. 54-92676

[51] Int. Cl.³ ...................... G01B 11/00; G01B 11/24
[52] U.S. Cl. .................................. 356/378; 356/237; 356/394
[58] Field of Search ........................ 356/378, 384–386, 356/394, 398, 241, 371, 446, 448, 237

[56] References Cited

U.S. PATENT DOCUMENTS

| 3,782,834 | 1/1974 | Fujimori et al. | 356/398 |
| 3,806,252 | 4/1974 | Harris et al. | 356/378 |
| 4,277,175 | 7/1981 | Karasaki et al. | 356/378 |

OTHER PUBLICATIONS

Habegger, M. A., "Optical Determination of Semiconductor Device Profiles", SPIE vol. 80, Developments in Semiconductor Microlithography, 1976, pp. 95–99.

Habegger, M. A., "Optical Determination of Semiconductor Device Edge Profiles", IBM Tech. Disc. Bull. vol. 19, #2, 7/1976, pp. 474–477.

Primary Examiner—William H. Punter
Attorney, Agent, or Firm—Antonelli, Terry & Wands

[57] ABSTRACT

In order to optically inspect wiring patterns on a printed wiring board, laterally travelling light rays are passed through a half reflecting mirror disposed above the printed wiring board so as to be directed downwardly, thereby illuminating a wiring surface of the printed wiring board with the light normal thereto and at the same time light is directed at a large incident angle to the wiring surface through, for example, optical glass fibers to illuminate the wiring surface, whereby a corner which is a part of the wall defining a plated through hole formed in the printed wiring board can be detected as an accurate optical image, thus ensuring a highly accurate inspection of the wiring patterns.

14 Claims, 17 Drawing Figures

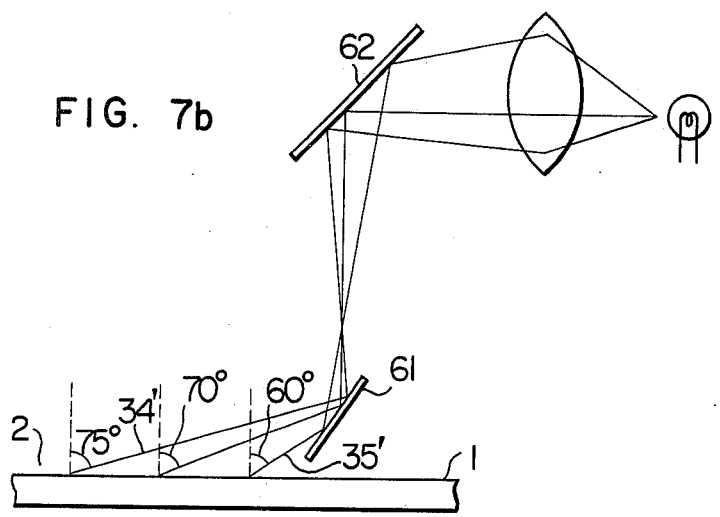
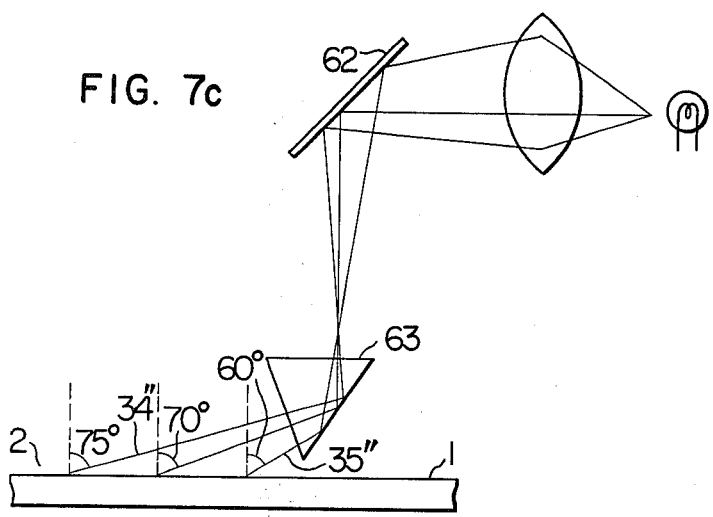
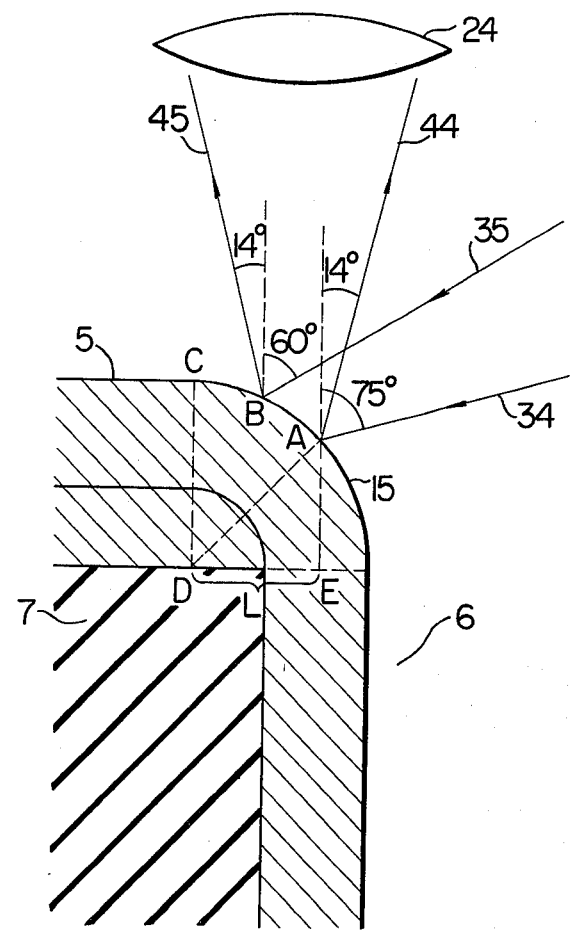

METHOD AND APPARATUS FOR INSPECTING PRINTED WIRING BOARDS

BACKGROUND OF THE INVENTION

Printed wiring boards generally have such a structure as shown in FIGS. 1 and 2 of the accompanying drawings. FIG. 1 is a plan view showing a wiring surface 2 of a printed wiring board 1, and FIG. 2 is a sectional view of the printed wiring board shown in FIG. 1, taken along the line II—II. In FIGS. 1 and 2, reference numerals 4 and 5 denote conductor pieces constituting a wiring pattern formed of a conductor foil such as a copper foil, 6 plated through holes for electrically connecting the wiring surface 2 with the back wiring surface 3, 7 an insulating substrate, and 13 and 14 conductor pieces constituting an internal layer pattern used respectively as ground and power layers and formed of a conductor foil such as a copper foil. The wiring pattern shown in FIG. 1 is formed by transferring a pattern which is indicated by solid lines (excepting heavy lines) and dotted lines in FIG. 1, on a copper foil in the form of an etching resist pattern by the use of a photographic plate (or a mask), and by etching the copper foil. When dust adheres to the photographic plate or a flaw is produced therein, there appear on the wiring pattern 2 a fine undesired pattern 8, a fine partial lack of pattern 9, and a fine projection 10. Further, the thickening 11 or thinning 12 of pattern is produced according as the etching operation is performed insufficiently or excessively. Such defects as above give rise to various problems. That is, the fine partial lack of pattern 9 and the thinning of pattern 12 increase the electric resistance of the pattern, decrease the current capacity of the pattern, and give rise to disconnection when the printed wiring board is subjected to slight rubbing. The fine undesired pattern 8, the fine projection 10 and the thickening 11 of pattern give rise to a short circuit, or a solder bridge in soldering process. As a result, a correct (or desired) wiring cannot be formed on the printed wiring board. Specifically, in a recent high density mounting which employs, for example, a pattern width of 0.1 mm, it is required to detect the above-mentioned defects without overlooking them. However, since such detection cannot be made by visual inspection, the apparatus shown in FIG. 3 is employed in which an optical image is formed for each of the printed wiring boards 1 to be inspected and another printed wiring board 1' for comparison and collation to be compared and collated with each other. The conventional method employing the above-mentioned apparatus will be explained below. In FIG. 3 which shows a conventional apparatus for inspection of printed wiring boards, the same structures are arranged on the right and left sides with the exception of electrical-signal collating device 27, and the part on the right side corresponding to each of the parts on the left side is given the same reference numeral with prime. Explanation will not be made on the function and operation of each part on the right side, because the explanation thereof is given by replacing a reference numeral by the same reference numeral with prime in the following explanation made on the function and operation of each part on the left side. Above the wiring surface 2 of the printed wiring board 1 are disposed a half reflecting mirror 23 which reflects the horizontal light from a light source 21 to produce the light incident upon the wiring surface 2, and through which the reflected light from the wiring surface 2 travels upward, a refractor 24 which converges the light having passed through the mirror 23 to form an optical image, and a photodiode array 25 which is placed in an image forming plane and converts a pattern of light and darkness in the formed image into a multiplicity of electrical signals 26. Further, a collating device 27 is provided in which both the electrical signals 26 delivered from the left photodiode array 25 and the electrical signals 26' delivered from a right-hand side photodiode array 25' are recognized as wiring patterns, and are compared and collated with each other to point out the presence or absence of defects or positions where the defects exist. The positioning of each of the printed wiring boards 1 and 1' is made by positioning means (not shown). Now, explanation will be made on a case where, for example, a printed wiring board shown in FIG. 4a is inspected. Referring to FIG. 3, the light emitted from the light source 21 is passed through a refractor 22 to form parallel rays, directed downward by the half reflecting mirror 23, and then incident upon various portions on the wiring surface 2 of the printed wiring board 1 as light rays 31, 32 and 33 shown in FIG. 4a. The light ray 31 is reflected back as the reflected light ray 41 of a low intensity level due to a low reflectivity of the insulating substrate 7, the light ray 32 is reflected back as the reflected light ray 42 of a high intensity level due to a high reflectivity of the wiring pattern 5 made of a metal such as copper, and the light ray 33 does not give rise to reflected light because it goes past to the back wiring surface 3 through the plated through hole 6 or a perforation. The reflected light rays 41 and 42 which are directed upward, are incident upon the surface of the photodiode array 25 through the half reflecting mirror 23 and the refractor 24 to form an optical image. The photodiode array 25 includes a multiplicity of fine photodiodes (or light receiving elements) which are arranged on a straight line. For example, 256 photodiodes are arranged on a straight line as long as 5 mm. FIG. 4b is a waveform chart for showing electrical signals generated by the individual photodiodes when the light rays 41 and 42 form the optical image. In FIG. 4b, the abscissa designates the location of each photodiode of the photodiode array 25, and the ordinate the level of each of the electrical signals. Further, reference symbol $I_1$ denotes the level of electrical signals corresponding to the position of the plated through hole 6, which is low due to the absence of reflected light, $I_2$ the level of electrical signals into which the reflected light from the insulating substrate 7 is converted, which level is low but higher than $I_1$, and $I_3$ the level of electrical signals into which the reflected light from the wiring pattern 5 is converted, which level is high. In order to facilitate the comparison of these levels, it is necessary for these three levels to be converted into two kinds of levels (light and dark levels) or binary levels. For this reason, there is provided a binary coder 28 which is formed of, for example, a voltage comparator, and which translates an electrical signal having a signal level higher than a level $I_s$ (shown in FIG. 4b) to the light level and an electrical signal of a signal level lower than the level $I_s$ to the dark level. Thus, the electrical signals based upon the wiring pattern 5 are translated to the light level (or "1" level of binary code), and those based upon the insulating substrate 7 and plated through hole 6 are translated to the dark level (or "0" level of binary code). That is, the electrical signals delivered from the photodiode array 25 are converted into binary signals. The binary signals thus obtained form linear information (that is, such linear information as viewing the pattern of FIG. 5a across the line $V_b$—$V_b$), since the light receiving surface of the photodiode array 25 has a form of a line. Accordingly, by storing these binary signals in a memory 29 while displacing the printed wiring board 1 in parallel in the plane containing the wiring surface 2, the plane information can be obtained. Then, the plane information on the wiring surface 2 and that on the wiring surface 2', both of which have been stored in the memory 29, are collated with each other at a pattern comparator 30 to indicate those parts which correspond to but are incongruous with each other, as a defect.

According to the above-mentioned inspecting apparatus, since the light rays 31 and 32 are incident upon the wiring surface 2 from above as shown in FIG. 4a, the reflected light rays 41 and 42 are directed upwardly as far as the wiring surface is flat, and positively converged by the refractor 24 to form an optical image, a light and dark pattern of which is converted to an electrical signal 26 by each photodiode in the photodiode array 25. The plated through holes 6 included in the wiring pattern usually expand at its opening portion on the wiring surface 2 so that the wall defining the hole has a corner 15 rounded at the opening portion, as shown in FIG. 2. As a result, the light incident upon the curved surface of the corner 15 cannot be reflected upwardly pursuant to the law of light ray reflection. Accordingly, the reflected light is not converged by the refractor 24, failing to take part in the production of pattern information and a diameter larger than that of an actual plated through hole is recognized. Therefore, the conventional inspecting apparatus in which light is incident upon the wiring surface from above is disadvantageously invalid for inspecting pattern information concerning the corner of the wall of the plated through hole, which corner is simply referred to as a plated through hole corner hereinafter.

To detail a defect at a plated through hole corner, reference is now made to FIGS. 5a and 5b. FIG. 5a is a plan view showing a wiring surface 2 of a printed wiring board 1, and FIG. 5b is a sectional view of the printed wiring board shown in FIG. 5a, taken along line $V_b$—$V_b$. In fabricating a printed wiring board by using an etching resist in the form of a dry film, a defect 16 at a plated through hole corner as shown in FIG. 5a often takes place when a dry film tent applied over the plated through hole for protecting the same is damaged during the etching treatment. The presence of the defect tends to cause troubles in soldering parts to the printed wiring board and breakage of the plated through hole corner.

SUMMARY OF THE INVENTION

The present invention contemplates elimination of the above drawbacks and has for its object to provide a method and an apparatus for inspecting printed wiring boards which can detect a defect at a plated through hole corner as well as other defects in the wiring pattern.

To accomplish the above object, the present invention is generally featured by, in addition to illuminating a wiring surface of a printed wiring board with light incident upon the wiring surface in the normal direction thereto, illuminating the wiring surface with light directed at a large incident angle to the wiring surface, that is, at an angle near 90° in terms of the incident angle with respect to the normal to the wiring surface, whereby reflected light rays from a curved surface of a plated through hole corner are directed upwardly, positively converged by a refractor to form an optical image, and a light and dark pattern of the optical image is converted to an electrical signal by a photodiode array.

BRIEF DESCRIPTION OF THE DRAWINGS

FIGS. 7a, 7b and 7c are diagrams showing details of the apparatus shown in FIG. 6.

FIG. 8 is a diagram for explaining the operation of the embodiment shown in FIG. 6.

DESCRIPTION OF THE PREFERRED EMBODIMENTS

Figure 3:
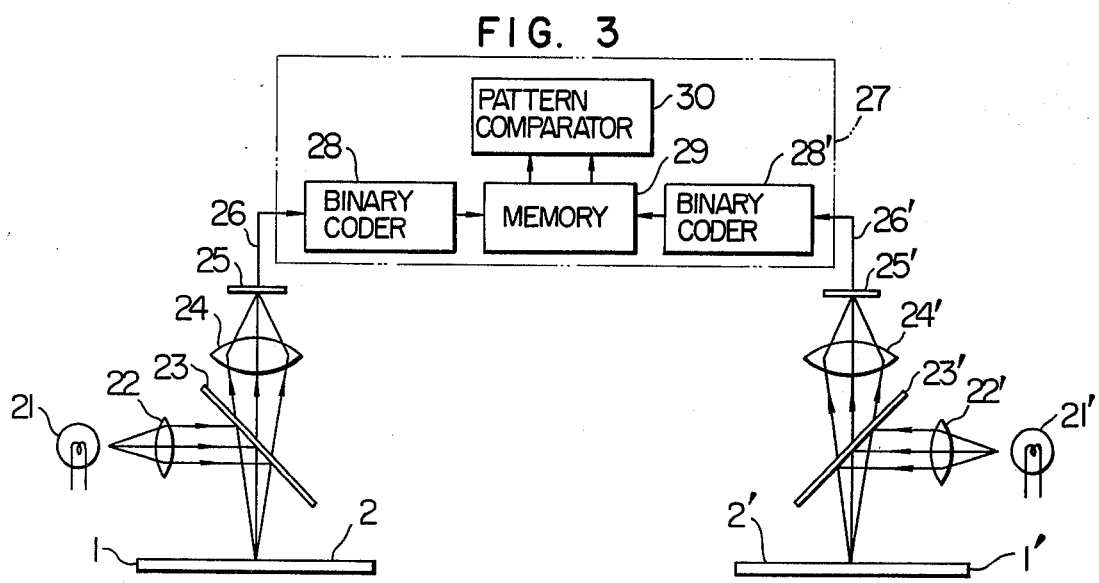
FIG. 3, FIG. 4a and FIG. 4b are diagrams useful for explaining a conventional apparatus for inspecting printed wiring boards.
Figure 4A:
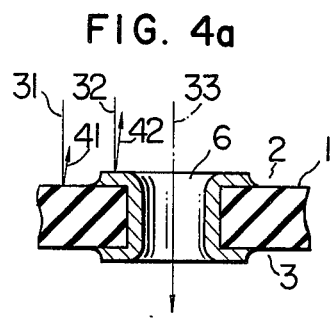
Figure 4B:
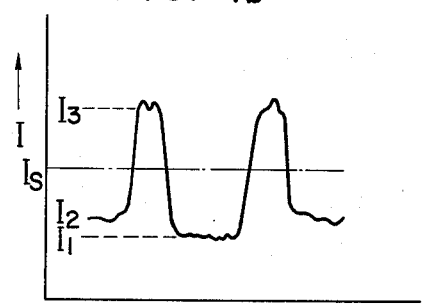
Figure 5A:
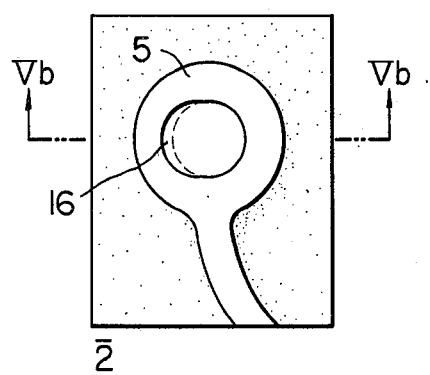
FIGS. 5a and 5b are diagrams useful for explaining a defect at a plated through hole corner.
Figure 5B:
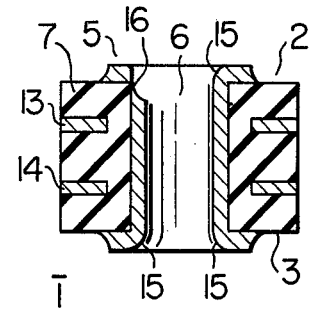
Figure 6:
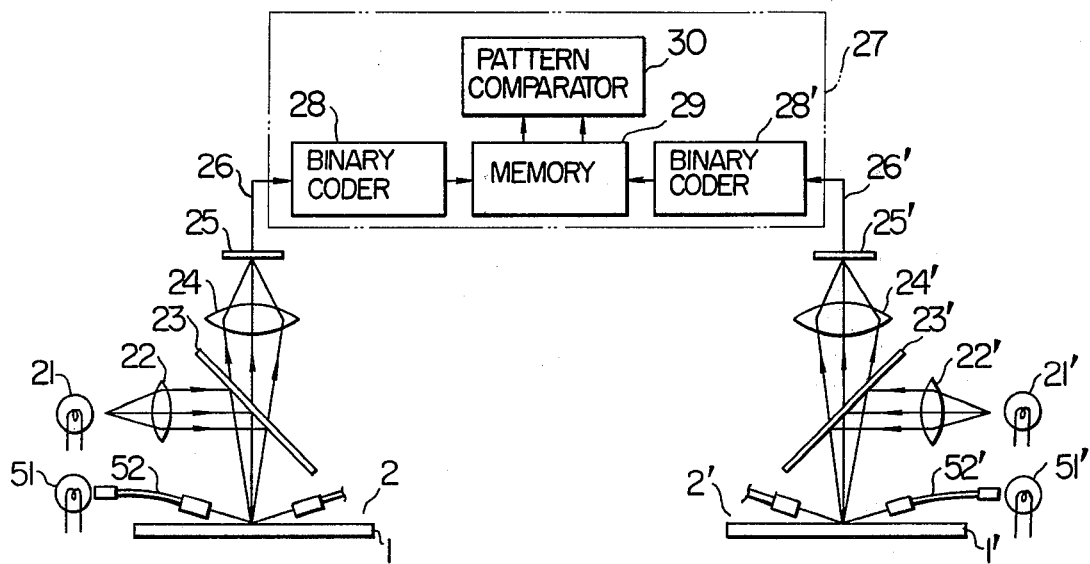
FIG. 6 is a schematic diagrammatic representation showing an embodiment of an apparatus for inspecting printed wiring boards according to the present invention.
Figure 7A:
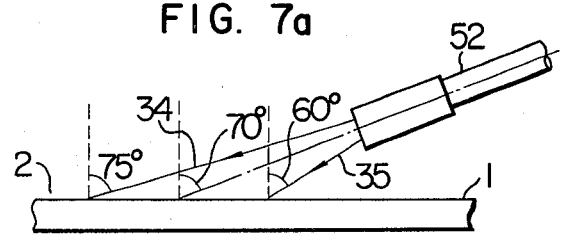

Referring first to FIG. 6 showing an apparatus for inspecting printed wiring boards embodying the invention, reference numerals 51 and 51' denote additional sources of light, independent of sources 21 and 21', which are disposed around a wiring surface 2 of a printed wiring board 1 to be inspected and a wiring surface 2' of a reference printed wiring board 1' and which are adapted to emit light for illuminating these wiring surfaces at a small angle with respect thereto that is, at a large incident angle, and 52 and 52' optical glass fibers for guiding the light emitted from the light sources 51 and 51' to inspection areas on the individual wiring surfaces 2 and 2'. A single light source may be provided serving as the sources 21 and 21'. Similarly, another light source may be provided serving as the sources 51 and 51'. Further, the wiring surfaces 2 and 2' may be illuminated at a large incident angle with light travelling through, for example, mirrors 61 and 62 as shown in FIG. 7b or mirror 62 and prism 63 as shown in FIG. 7c, without resort to the optical glass fibers 52 and 52'. Explanation will not be made on elements 21 to 26, 21' to 26', 27, 28, 28', 29 and 30 which correspond to like elements in FIG. 3. In FIG. 7a light from the optical glass fiber 52 is a pencil of light rays having a central light ray (illustrated at chained line) at an incident angle of about 70° and outer light rays 34 and 35 at incident angles of 75° and 60°, and is incident upon the wiring surface 2 of the printed wiring board 1. Similarly, in FIGS. 7b and 7c, the incident light pencils have central light ray at 70° and outer light rays 34', 34" and 35', 35" at 75° and 60°, respectively. In order to obtain pattern information from as large an area of the plated through hole corner as possible, it is desirable to illuminate the wiring surface 2 with light at an incident angle as close to 90° as possible. But an appreciable gap or space from the wiring surface is required for arranging fixture tools or jigs for the printed wiring board 1 and other elements of the inspection apparatus so that an incident angle of about 70° is exemplified in FIGS. 7a, 7b and 7c.

Figure 1:
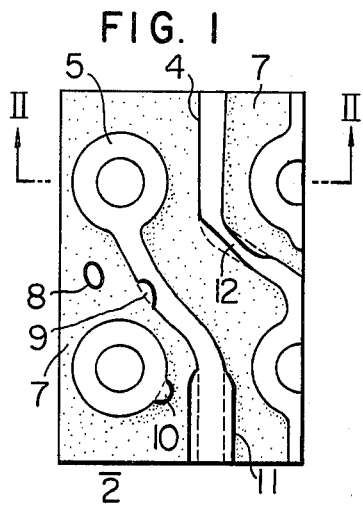
FIG. 1 is an enlarged plan view showing a part of a general printed wiring board.
Figure 2:
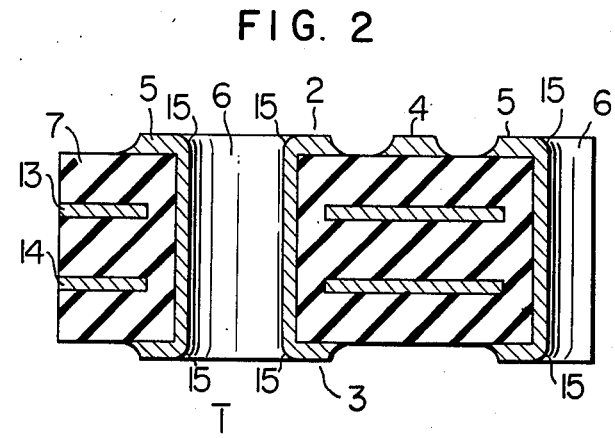
FIG. 2 is a sectional view taken along line II—II in FIG. 1.

The operation will now be described with reference to FIG. 8 which illustrates, in enlarged sectional form, the plated through hole corner 15 and its neighbourhood of the printed wiring board shown in FIG. 2 with a metal conductor such as of copper hatched. Incident light rays 34 and 35 which are identical to those shown in FIG. 7a are at angles 75° and 60° as measured from vertical lines shown at dotted lines passing the incident points A and B on the plated through hole corner 15. The light rays 34 and 35 are reflected at the plated through hole corner 15 and reflected light rays 44 and 45 are directed to the refractor 24. It will be appreciated that the reflected light rays 44 and 45 are such as deviating from the vertical lines by an angle of 14° since the refractor 24 being constituted by a lens of 85 mm F/1.0 in the embodiment has a field angle of 14°, when used at a magnification of 1 (one).

In this manner, in contrast to the conventional inspecting apparatus which employs only the incident light normal to the wiring surface and hence permits generation of pattern information regarding only a flat surface portion of the wiring pattern 5 which surface portion terminates at a point C preceding the curved surface of the plated through hole corner 15, generation of pattern information can be extended by the light illumination at a large incident angle of the wiring surface according to the present invention, covering the area including an intermediate point A on the plated through hole corner 15. Accordingly, when the wiring pattern is projected upon a boundary plane between the metal conductor and the insulating substrate 7, it is possible to obtain pattern information covering region L between a point D resulting from projecting point C upon the boundary plane and a point E resulting from projecting point A upon the plane, thereby ensuring that a defect at the plated through hole corner can be detected. Thus, the collating device 27 (FIG. 6) which is positioned on the same side of the printed wiring boards as the illuminating arrangements serves for recognizing a plane configuration of the corner as projected upon the horizontal plane by receiving the reflected light rays.

Figure 9A:
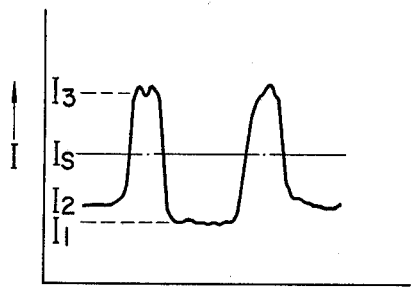
FIGS. 9a, 9b, 9c, 10 and 11 are graphic representations useful for explaining electrical signals generated in the apparatus shown in FIG. 6.
Figure 9B:
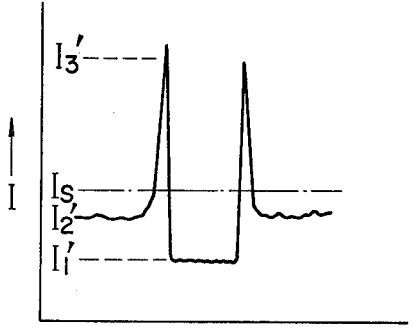
Figure 9C:
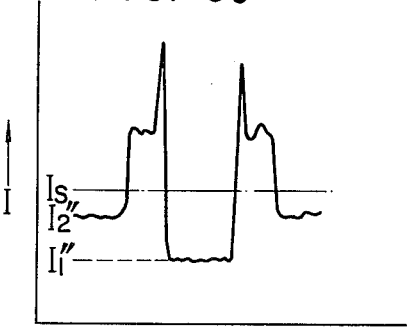

FIGS. 9a, 9b and 9c are waveform charts for showing electrical signals generated corresponding to optical images formed on the photodiode array 25. In these drawings, the abscissa designates the location of each photodiode of the photodiode array 25 and the ordinate the level of each of the electrical signals. Specifically, FIG. 9a shows an electrical signal generated by the photodiode array 25 when illuminating the wiring surface only with light normal thereto with the conventional inspecting apparatus, FIG. 9b shows an electrical signal generated by the photodiode array 25 in accordance with light illumination at a small angle with respect to the wiring surface (i.e., at a large incident angle) featuring the present invention, and FIG. 9c shows an electrical signal generated by the photodiode array 25 in the inspecting apparatus of the present invention in accordance with the illumination with the normal incident light and the illumination with the lateral light directed to the wiring surface at a large incident angle in combination. Accordingly, the electrical signal shown in FIG. 9c represents a sum of the electrical signals of FIG. 9a and FIG. 9b. Reference symbols $I_1$, $I_1'$ and $I_1''$ denote the levels of electrical signals corresponding to the position of the plated through holes, which are identical due to the absence of reflected light and related as, $$I_1 = I_1' = I_1''.$$

Reference symbols $I_2$, $I_2'$ and $I_2''$ denote the levels of electrical signals to which the reflected light rays from the insulating substrate 7 are converted, and $I_2'$ and $I_2''$ are almost equal, i.e., $$I_2' \approx I_2''.$$

The electrical signal level $I_2$ is lower than the electrical signal levels $I_2'$ and $I_2''$ because the insulating substrate 7 has surface irregularity of the order of 10 to 15 microns so that the incident light rays at a large incident angle are scattered and converged by the refractor 24 so as to be sensed by the photodiode array 25. Reference symbol $I_3$ denotes the level of electrical signal corresponding to the position of the wiring pattern and $I_3'$ the level of electrical signal corresponding to the plated through hole corner. The electrical signal level $I_3'$ is higher than the electrical signal level $I_3$ because the surface irregularity of the plated through hole corner is smaller than that of the wiring pattern so that scattered reflection is suppressed.

Figure 10:
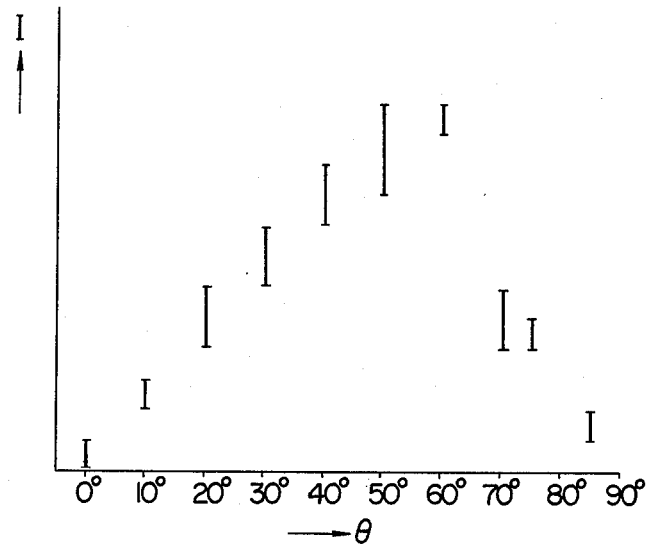

FIG. 10 shows dependency of the electrical signal level corresponding to the insulating substrate upon the incident angle of light illuminating the wiring surface. In FIG. 10, the ordinate represents electrical signal level I corresponding to the insulating substrate and the abscissa represents incident angle $\theta$ of light illuminating the wiring surface. It will be seen from FIG. 10 that when the wiring surface is illuminated with the light from above, that is, when the incident angle $\theta$ of light approximates 0°, the electrical signal level corresponding to the insulating substrate is low but as the incident angle $\theta$ increases, the level goes higher and reaches a maximum at 60° and is then lowered. Accordingly, it is understood that when the wiring surface is illuminated with the light at a large incident angle directed thereto, that is, when the incident angle $\theta$ of light approximates 90°, the electrical signal level corresponding to the insulating substrate is also low. Since high values of the electrical signal level corresponding to the insulating substrate are indistinguishable from the electrical signal level corresponding to the wiring pattern, for such high levels, the binary-level conversion by the binary coder is invalid wherein the electrical signals based upon the wiring pattern are converted to the light level (or "1" level of binary code) and those based upon the insulating substrate are converted to the dark level (or "0" level of binary code). Therefore, it is necessary to utilize the electrical signal level corresponding to the insulating substrate which is as low as possible and in this sense, the light illumination at a small angle with respect to the wiring surface, preferably, at an incident angle $\theta$ of 70° to 90° is advantageous.

Figure 11:
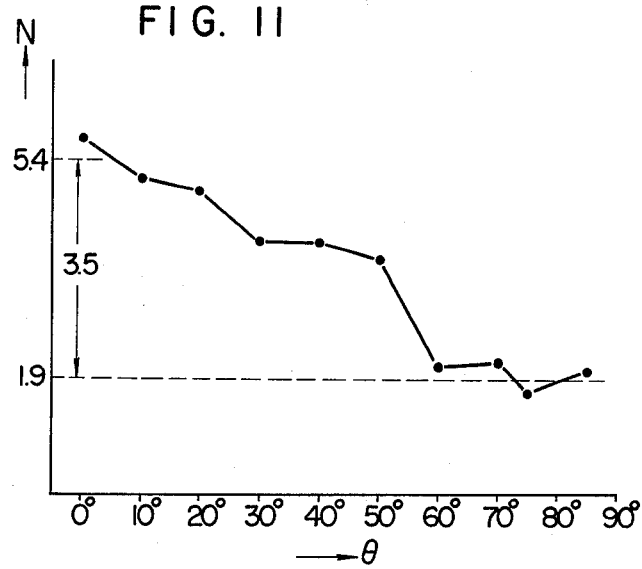

FIG. 11 shows the relation between the incident angle of light illuminating the wiring surface and the average gradient with which electrical signals representative of optical images of a wiring pattern rise from the electrical signal level ($I_1$, $I_1'$) for the plated through hole to the signal level ($I_3$, $I_3'$) for the wiring pattern. In FIG. 11, the ordinate represents the number N of electrical signals observed for a unit voltage, and the abscissa represents the incident angle $\theta$ of light illuminating the wiring surface. Here, reference will be briefly made to "the number of electrical signals observed for a unit voltage". The number of electrical signals means the number of bright spots observed on a display screen such as of a synchroscope and corresponding to individual electrical signals produced by photodiodes of the photodiode array having received optical inputs. The photodiodes are arranged with a fixed spacing of, e.g., 20 μm. The illustration in FIGS. 9a, 9b and 9c results from a collection of such bright spots observed on the screen as mentioned above and the amplitude may represent the output voltage of the photodiodes. Thus, a number of the bright spots can be determined for a unit length of the amplitude, i.e., for a unit voltage and this number of the bright spots or the number of the electrical signals for a unit voltage indicates the gradient of a waveform of the electrical signal corresponding to an optical image of the wiring pattern. If the number for a unit voltage is large the gradient is small while if the number for a unit voltage is small the gradient is large. It will be seen from FIG. 11 that when the wiring surface is illuminated with light from above, that is, when the incident angle $\theta$ of light approximates 0°, the number N of electrical signals for a unit voltage is large so that the electrical signal rises with a small gradient whereas as the incident angle of light illuminating the wiring surface increases, the number of the electrical signals for a unit voltage decreases so that the electrical signal rises with a steep gradient. For the case of FIG. 9a, the number of electrical signals for a unit voltage amounts to an average of 5.4 in order that the electrical signal rises from the electrical signal level $I_1$ for the position of the plated through hole to that $I_3$ for the wiring pattern. For the case of FIG. 9b, the number of individual electrical signals amounts to an average of 1.9 in order that the electrical signal rises from the electrical signal level $I_1'$ for the position of the plated through hole to that $I_3'$ for the plated through hole corner. Accordingly, the difference is 3.5, representing information regarding the plated through hole corner and which is obtained based on the light illumination at a large incident angle directed to the wiring surface. This difference is converted to a dimensional length of $20 \times 3.5 = 70$ μm when the pitch or the spacing between adjacent photodiodes is 20 μm. In the above discussion, electrical conditions are $I_1$, $I_1' = 0$ V, $I_s = 1$ V, and $I_3$, $I_3' = 2$ V.

Thus, the detection of the plated through hole corner can be enhanced by 70 μm by the light illumination at a large incident angle directed to the wiring surface, which means that the diameter of the plated through hole detected by the inspecting apparatus of the present invention may be smaller than that detected by the conventional apparatus by 70 μm, thereby ensuring recognition of an approximately actual diameter.

As has been described, the present invention advantageously employs the light illumination at a large incident angle directed to the wiring surface to obtain pattern information from the plated through hole corner so that the approximately actual diameter of the plated through hole can be recognized and the defect at the plated through hole corner can be detected.

I claim:

1. An apparatus for inspecting printed wiring boards wherein a wiring pattern on a printed wiring board is inspected by detecting light reflected from a wiring surface of the printed wiring board, said apparatus comprising:
   first illuminating means for illuminating the wiring surface of the printed wiring board with light substantially normal to the wiring surface;
   second illuminating means for illuminating the wiring surface of said printed wiring board with light at a large incident angle; and
   means for deciding whether a defect exists in a wiring pattern on said wiring surface by receiving the light reflected from said wiring surface as a result of the light illumination by the first and second illuminating means.

2. An apparatus according to claim 1, wherein said second illuminating means includes light transmission means through which the light rays are directed to the wiring surface of the printed wiring board.

3. An apparatus according to claim 2, wherein said light transmission means includes optical glass fibers.

4. An apparatus according to claim 2, wherein said light transmission means includes a prism arranged to direct the light to the wiring surface of the printed wiring board.

5. An apparatus according to claim 2, wherein said light transmission means includes mirrors arranged to direct the light to the wiring surface of the printed wiring board.

6. An apparatus according to claim 1, wherein the said incident angle is not smaller than 70° and smaller than 90°.

7. An apparatus according to claim 1, wherein said second illuminating means has such a structure as for illuminating the wiring surface with the light from a plurality of positions around said wiring surface.

8. An apparatus according to claim 1, wherein said deciding means receives the reflected light from the wiring surface which are directed upwardly.

9. An apparatus for inspecting a printed wiring board having a wiring pattern formed on a wiring surface of the printed wiring board and at least one plated through hole, said plated through hole being formed in the direction of thickness of the printed wiring board said through hole expanding at its opening portion outwardly so that the wall defining the hole has a rounded corner at said opening portion, said apparatus comprising:
   means for illuminating said wiring surface and said corner of the wall of said plated through hole with light incident substantially normal to and at a large incident angle such that light reflected from said wiring surface and said corner is directed upwardly; and
   means positioned on the same side of said printed wiring board as said illuminating means for recognizing by receiving the reflected light rays in a direction normal to the printed wiring board a plane configuration of the wiring pattern and the corner as projected upon the horizontal plane.

10. A method for inspecting printed wiring boards wherein a wiring pattern on a printed wiring board is inspected by detecting light reflected from a wiring surface of the printed wiring board, said method comprising the steps of:
   illuminating the wiring surface of a printed wiring board to be inspected with light substantially normal to and at a large incident angle;
   receiving light reflected from said wiring surface to form an optical image;
   converting the optical image to an electrical signal;
   translating the electrical signal to a binary signal;
   obtaining a similar binary signal from a printed wiring board to be used as a reference and storing these two kinds of binary signals separately; and comparing and collating the contents stored separately.

11. An apparatus according to claim 1, wherein said incident angle is not smaller than 60° and is smaller than 90°.

12. An apparatus according to claim 9, wherein said large incident angle is not smaller than 60° and is smaller than 90° with respect to the normal to said wiring surface.

13. An apparatus according to claim 9, wherein said large incident angle is not smaller than 70° and is smaller than 90° with respect to the normal to said wiring surface.

14. An apparatus according to claim 9, wherein said illuminating means includes first means for illuminating the wiring surface of the printing wiring board with light substantially normal to the wiring surface, and second means for illuminating the wiring surface of the printed wiring board with light at said large incident angle.

* * * * *